US00PP15557P2

(12) United States Plant Patent
Zaiger et al.

(10) Patent No.: US PP15,557 P2
(45) Date of Patent: Feb. 15, 2005

(54) PEACH TREE NAMED 'KLAMATH'

(50) Latin Name: *Prunus persica*
Varietal Denomination: Klamath

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/734,898

(22) Filed: Dec. 15, 2003

(51) Int. Cl.[7] ..... A01H 5/00
(52) U.S. Cl. ..... Plt./197
(58) Field of Search ..... Plt./197

*Primary Examiner*—Kent Bell
*Assistant Examiner*—S. B. McCormick-Ewoldt

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular production of large size fruit.
2. Fruit with firm, non-melting flesh suitable for mechanical pitters.
3. Maintains excellent fruit shape after being canned.
4. Relatively uniform fruit maturity throughout the tree.
5. Fruit with good flavor fresh as well as canned.
6. The tree with vigorous, upright growth.

1 Drawing Sheet

Genus and Species: *Prunus persica.*

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

2. Prior Varieties

Among the existing varieties of peach and nectarine trees, which are known to us, and mentioned herein, 'Carolyn' Peach (non-patented), 'Loadel' Peach (non-patented), 'Andross' Peach (non-patented) and 'Royal Giant' Nectarine (U.S. Plant Pat. No. 4,107).

Statement Regarding Federally Sponsored Research and Development: Not applicable.

Origin of the Variety:

The new and distinct variety of peach tree (*Prunus persica*) was developed by us in our experimental orchard located near Modesto, Calif., as a first generation seedling from seed of a cross between proprietary lines of immediate parents with field identification numbers 8EB258 and 40GC250. The maternal parent (8EB258) originated from a first generation cross between 'Carolyn' Peach (non-patented) and 'Loadel' Peach (non-patented). The paternal parent (40GC250) originated from a cross between 'Royal Giant' Nectarine (U.S. Plant Pat. No. 4,107) and a canning cling peach of unknown parentage. We planted and maintained under close and careful observation, a large number of these first generation seedlings on their own root system, during which time we recognized the desirable tree and fruit characteristics of the present variety and selected it in 1989 for asexual propagation and commercialization.

Asexual Reproduction of the Variety:

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree is of large size, vigorous, upright growth and a regular and productive bearer of large size, non-melting, yellow flesh, clingstone fruit with very firm flesh, good handling and shipping quality. The fruit is further characterized by maturing relatively uniform throughout the tree, and maintaining excellent shape, texture, color and appearance after being canned. The new variety differs from its maternal parent (8EB258) by having firmer flesh and maturing approximately 14 days earlier. The new variety differs from its paternal parent (40GC250), which is a nectarine by being a peach. In comparison to 'Andross' Peach (non-patented), the tree of the new variety has more vigor, heavier production of firmer, non-melting, yellow flesh fruit with greater resistance to bruising and browning, and is 1 to 2 days earlier in maturity. The fruit after canning has less internal breakdown, is firmer with a more attractive appearance.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, Calif., with color in accordance with Munsell Book of Color.

Tree

*Size.*—Large. Pruned to 3 to 3.5 meters in height at maturity for economical harvesting of fruit.

*Vigor.*—Vigorous. Growth of 1.5 to 2 meters the first growing season. Varies with soil fertility, climatic conditions and cultural practices.

*Form.*—Upright, usually pruned to vase shape.

*Branching habit.*—Upright. Crotch angle approximately 30°. Heavy fruit production increases crotch angle.

*Productivity.*—Productive, thinning and spacing of fruit necessary to develop desired marketable size.

*Bearer.*—Regular, has had adequate fruit set for 5 consecutive years. No alternate bearing observed.

*Fertility.*—Self fertile.

*Density.*—Medium dense. Usually pruned to vase shape to increase sunlight and air movement to center of tree.

*Hardiness.*—Hardy in all fruit growing areas of California. Approximate winter chilling requirement 800 hours at or below 45° F.

Trunk

*Size.*—Large, stocky. Average circumference 46.8 cm measured 31.2 cm above ground.

*Texture.*—Medium, shaggy, roughness increases with age.

*Color.*—Varies from 2.5Y 6/2 to 2.5Y 5/2, darkens with age.

Branches

*Size.*—Medium. Average circumference 18.2 cm at 1.3 meters above ground.

*Surface texture.*—New growth smooth, mature growth medium rough.

*Lenticels.*—Average number of 22 in a 25.8 square cm section. Average length 3.3 mm. Average width 1.5 mm. Color varies from 5YR 6/8 to 7.5YR 5/8.

*Color.*—Varies from 5Y 6/10 on new growth to 5YR 4/8 on mature growth.

Leaves

*Size.*—Large. Average length 136.0 mm. Average width 37.3 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentations over midrib and leaf veins, glabrous. Lower surface relatively smooth with small ridges created by midrib and pinnate venation, glabrous.

*Petiole.*—Medium size. Average length 9.7 mm. Average width 1.5 mm. Longitudinally grooved. Color 2.5GY 7/8.

*Glands.*—Reniform. Medium to large size. Average length 1.0 mm. Average width 0.6 mm. Average number 2, varies from 1 to 3. Primarily located on upper portion of petiole and base of leaf blade. Color varies from 2.5Y 6/6 to 2.5Y 6/6 on upper surface of glands.

*Color.*—Upper surface varies from 2.5GY 4/4 to 5GY 5/4. Lower surface varies from 2.5GY 6/4 to 5GY 7/6. Midvein color 2.5GY 8/6.

Flower buds

*Size.*—Medium, non-showy. Average length 12.6 mm. Average diameter 6.6 mm.

*Hardiness.*—Hardy in all stone fruit growing areas of California.

*Form.*—Plump, conical, becoming oblongated before opening.

*Pedicel.*—Average length 4.2 mm. Average width 2.0 mm. Color 2.5GY 7/8.

*Color.*—Varies from 5RP 6/10 to 5RP 6/12.

Flowers

*Size.*—Medium, non-showy. Average height 16.9 mm. Average diameter 20.0 mm.

*Petals.*—Number — 5, alternately arranged to sepals. Shape — oblanceolate. Average length 11.8 mm. Average width 6.2 mm. Margin — entire. Color varies from 5RP 6/12 to 5RP 8/6, the outer surface of the petals darken in color.

*Sepals.*—Number — 5, alternately arranged to petals. Shape — triangular, apex rounded. Average length 4.0 mm. Average width 3.7 mm. Color — upper surface 10Y 5/6, glabrous, lower surface 7.5RP 3/8, pubescent.

*Stamens.*—Average number per flower 43. Average filament length 12.4 mm. Filament color N 9.5/ when flower first opens, becoming 2.5RP 6/10 as flower ages. Color of anthers 6.25R 3/12.

*Pollen.*—Self fertile. Color — 2.5Y 8/8.

*Pistil.*—Normally 1, varies from 1 to 2. Average length 14.7 mm. Surface — pubescent. Color 2.5GY 9/6. Stigma approximately 2.4 mm above anthers.

*Fragrance.*—Slight.

*Blooming period.*—Date of First Bloom Mar. 5, 2003. Date of Petal Fall Mar. 14, 2003. Varies slightly with climatic conditions.

*Color.*—Varies from 5RP 8/2 to 5RP 6/2, outer edges of petals much darker in color than center of petals.

*Number flowers per flower bud.*—One.

*Pedicel.*—Average length 4.4 mm. Average width 2.2 mm. Color 2.5GY 7/6.

Fruit

*Maturity when described.*—Firm ripe.

*Date of first picking.*—Aug. 1, 2003.

*Date of last picking.*—Aug. 6, 2003. Varies slightly with climatic conditions.

*Size.*—Large. Average diameter axially 77.5 mm. Average transversely in suture plane 84.1 mm. Average weight 311.7 grams, average weight varies slightly with fertility of the soil, amount of thinning and climatic conditions.

*Form.*—Globose.

*Suture.*—Nearly smooth, extends from base to apex.

*Ventral surface.*—Very slightly lipped.

*Apex.*—Varies from rounded to slight tip.

*Base.*—Retuse.

*Cavity.*—Rounded to slightly elongated in suture plane. Average depth 6.1 mm. Average breadth 11.6 mm.

Stem

*Size.*—Medium. Average length 7.1 mm. Average diameter 3.6 mm.

*Color.*—10Y 7/6.

Flesh

*Ripens.*—Evenly.

*Texture.*—Firm, non-melting.

*Fibers.*—Few, small, tender.

*Firmness.*—Firm flesh, higher degree of firmness compared to the standard canning peach 'Andross' (non-patented).

*Aroma.*—Slight.

*Amydgalin.*—Undetected.

*Eating quality.*—Good fresh, very good canned.

*Flavor.*—Good, comparable to other standard non-melting canning peach varieties.

*Juice.*—Moderate.

*Brix.*—Average 13.7°, varies slightly with amount of fruit per tree and climatic conditions.

*Color.*—Varies from 2.5Y 8/10 to 2.5Y 8.5/10. Pit cavity 2.5Y 8/8. No bleeding from pit cavity into flesh.

Skin

*Thickness.*—Medium.

*Surface.*—Smooth.

*Down.*—Moderate amount and length.

*Tendency to crack.*—None.

*Color.*—Ground color varies from 2.5Y 8/10 to 2.5Y 8.5/10. Very slight blush 7.5R 4/10 to 7.5R 4/12 on 1 to 5% of skin surface.

*Tenacity.*—Tenacious to the flesh.

*Astringency.*—None.

Stone

*Type.*—Clingstone.

*Size.*—Large. Average length 40.4 mm. Average width 30.2 mm. Average thickness 24.0 mm.

*Form.*—Ovoid.

*Base.*—Straight.

*Apex.*—Pointed. Average length 2.1 mm.

*Surface.*—Irregularly furrowed toward the apex, pitted throughout with deeper pits toward base. Pits vary from rounded to elongated. Usually one long furrow on each side of suture.

*Sides.*—Unequal, with one side extending further from suture plane.

*Ridges.*—Relatively wide and slightly rough.

*Tendency to split.*—None.

*Color.*—Varies from 5YR 5/6 to 5YR 3/6 when dry.

Kernal

*Form.*—Ovate.

*Taste.*—Bitter.

*Viability.*—Viable, embryo completely developed.

*Size.*—Large. Average length 20.2 mm. Average width 13.6 mm. Average thickness 6.4 mm.

*Skin.*—Color — 5Y 9/6 when dry.

Use

Canning.

Keeping quality: Good, held firm in cold storage 3 weeks at 38° to 42° F. with minimal loss of firmness or internal flesh breakdown.

Shipping quality: Good, minimal skin scarring or bruising of flesh during picking and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth and a regular and productive bearer of large, very firm, non-melting, yellow flesh, clingstone fruit, which after being canned maintains excellent fruit shape, texture and appearance with good flavor and eating quality, and in comparison to the canning variety 'Andross' Peach (non-patented), the new variety has firmer flesh, greater resistance to bruising and browning, more attractive appearance after being canned and is 1 to 2 days earlier in maturity.

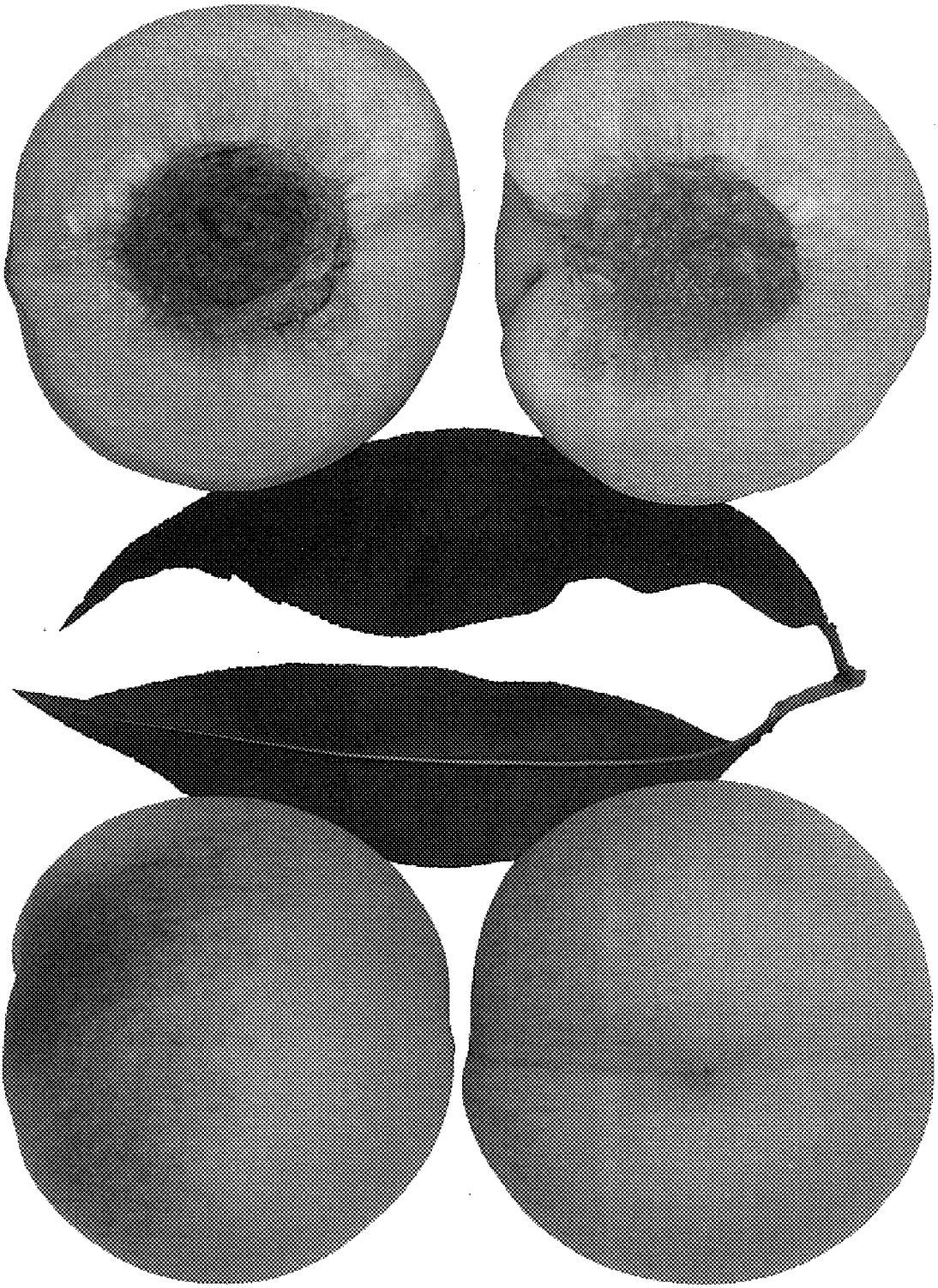

* * * * *